United States Patent [19]

Cozzi et al.

[11] Patent Number: 5,386,072
[45] Date of Patent: Jan. 31, 1995

[54] PROCESS FOR THE PREPARATION OF LINEAR ALKYLBENZENES

[75] Inventors: Pierluigi Cozzi, Nerviano; Giuseppe Giuffrida, Caronno Pertusella; Tullio Pellizzon, Paderno Dugnano; Pierino Radici, Turate, all of Italy

[73] Assignee: Enichem Augusta S.p.A., Palermo, Italy

[21] Appl. No.: 10,816

[22] Filed: Jan. 29, 1993

[30] Foreign Application Priority Data

Feb. 3, 1992 [IT] Italy .................... MI92 A 00201

[51] Int. Cl.$^6$ .................... C07C 2/66; C07C 2/70; C07C 2/64
[52] U.S. Cl. .................... 585/456; 585/455; 585/459; 585/462; 585/469
[58] Field of Search .............. 585/455, 456, 459, 462, 585/469

[56] References Cited

U.S. PATENT DOCUMENTS

| | | | |
|---|---|---|---|
| 3,401,208 | 9/1968 | Kerfoot et al. | 585/459 |
| 3,674,885 | 7/1972 | Griesinger et al. | 585/456 |
| 3,678,123 | 5/1972 | Boggs | 585/455 |

FOREIGN PATENT DOCUMENTS 1275037  8/1968  Germany .

OTHER PUBLICATIONS

Chemical Abstracts, vol. 85, No. 17, 25 Oct. 1976; abstract No. 123543s, p. 609.
Chemical Abstracts, vol. 96, No. 2, Jan. 1982, abstract No. 19796t, p. 421.

Primary Examiner—Asok Pal
Assistant Examiner—E. D. Irzinski
Attorney, Agent, or Firm—Hedman, Gibson & Costigan

[57] ABSTRACT

Process for the preparation of linear alkylbenzenes, wherein the benzene is reacted, in the presence of aluminum chloride or aluminum in powder form, with a mixture composed of $C_7$–$C_{20}$ n-olefins and $C_7$–$C_{20}$ chloroparaffins, with a molar ratio n-olefins/chloroparaffins between 70:30 and 99:1.

10 Claims, No Drawings

PROCESS FOR THE PREPARATION OF LINEAR ALKYLBENZENES

The present invention relates to a process for the preparation of linear alkylbenzenes, in particular of linear alkylbenzenes wherein the alkyl is composed of a linear paraffinic chain, containing from 7 to 20 carbon atoms. These products, as is known, are widely used on an industrial scale for the synthesis, by sulfonation, of biodegradable surface-active agents.

Alkylbenzenes having the alkyl substituent composed of a linear paraffinic chain (usually identified with the abbreviation LAB) are normally prepared, industrially, by the chlorination of linear paraffins, the catalytic alkylation of benzene using the chlorinated paraffins thus obtained, in the presence of aluminum chloride or aluminum in powder form, the separation of the catalyst to obtain, by distillation, the alkylated product. The use of aluminum in powder form instead of aluminum chloride is made possible by the fact that during the reaction between chloroparaffins and benzene, hydrochloric acid is produced, which reacts with the aluminum to form aluminum chloride and at the same time acts as co-catalyst. The separation of the catalyst from the raw alkylation products can be carried out by decanting, in that during the reaction a complex-compound is formed between the catalyst and the hydrocarbons, generally called "hydrocarbon catalytic complex", which is basically insoluble in the reaction mixture.

This process has numerous disadvantages, mainly connected with the formation of undesired products, such as tetralins and other branched compounds which are difficult to separate and which, as well as reducing the yield of linear alkylbenzene, also cause a lowering of the biodegradability of the surface-active agents obtained after the sulfonation. There is also the formation of considerable quantities of products with a high boiling-point, which remain as residues of the final distillation and can only be partly recycled in the alkylation reaction.

As an alternative to alkylation with chloroparaffins, another known method is to prepare linear alkylbenzenes by the catalytic alkylation of benzene with n-olefins, in the presence, as catalysts, of Lewis acids, such as, for example, aluminum chloride, boron trifluoride, hydrofluoric acid, sulphuric acid, phosphoric anhydride, etc. In industrial practice, aluminum chloride or hydrofluoric acid are normally used, the one latter necessitating the use of special systems to guarantee the safety of the plants, with a consequent increase of production costs.

With respect to alkylation with chloroparaffins, the use of n-olefins precludes the possibility of using aluminum in powder form as catalyst, this being less costly product which is also easier to handle than aluminum chloride.

A further disadvantage arising from the use of n-olefins as alkylating agents consists of the difficulty of separating the consumed catalyst from the final products. In fact, contrary to the process in which chloroparaffins are used, during the alkylation the aluminum chloride forms a hydrocarbon catalytic complex which is soluble in the reaction mixture. This makes it necessary to have a subsequent phase for the purification of the crude alkylated mixture, by washing with aqueous solutions of hydrochloric acid and/or sodium hydroxide, before distillation. However carefully this purification may be carried out, the colour of the product going to distillation is much darker than that of the alkylated product obtained from chloroparaffins. This drawback makes it necessary to have a further decolouring treatment of the high-boiling products obtained as a distillation residue, usually re-utilized for the preparation of lubricating oils. The necessity of having this decolouring treatment makes the re-use of the high-boiling products inconvenient from an economical point of view.

It has now been found that by using a particular mixture of n-olefins and chloroparaffins as the alkylating agent of benzene, in the presence of aluminum chloride or aluminum in powder form as catalyst, it is possible to significantly reduce the formation of sub-products, such as tetralins, branched alkylbenzenes and high-boiling products, with considerable advantages as regards the purity and linearity of the final product as well as the total yield of the process.

The present invention consequently relates to a process for the preparation of linear alkylbenzenes wherein the benzene is reacted in the presence of a catalyst selected from aluminum chloride or aluminum in powder form, with a mixture basically composed of n-olefins having from 7 to 20 carbon atoms and chloroparaffins having from 7 to 20 carbon atoms wherein the molar ratio n-olefins/chloroparaffins is between 70:30 and 99:1.

In a preferred form of practice, the chloroparaffins are obtained by the partial chlorination of the corresponding paraffins, as described, for example, in U.S. Pat. No. 3,584,066. To obtain the maximum yield in monochloroparaffins, this chlorination is carried out with a high molar ratio paraffins/chlorine, and consequently a mixture of chlorinated paraffins and non-chlorinated paraffins is obtained. Owing to the difficulties of separation, this mixture is usually sent directly to the alkylation reactor. The non-chlorinated paraffins, which remain unaltered during the alkylation, can be subsequently recovered during the distillation of the alkylation products and recycled in the chlorination stage.

The n-olefins are generally prepared, on an industrial scale, by the dehydrogenation of the corresponding paraffins in the presence of catalysts composed of noble metals, for example, platinum, supported on inert materials, such as alumina. The dehydrogenation reaction is partial, and consequently a mixture of olefins and paraffins is obtained at the outlet of the reactor, and the n-olefins are isolated by means of an extraction process with molecular sieves. One of the most widely used processes of this kind on an industrial scale is called Pacol-Olex ® (see, for example: "Handbook of Petroleum Refining Processes", Robert A. Meyers Ed., McGraw-Hill, Inc., New York, 1986; or: D. B. Broughton, "Absorptive Separations—Liquids", Kirk-Othmer Encyclopedia of Chemical Technology, Vol. 1, 3a ed., John Wiley & Sons, New York, 1978; or also: R. C. Berg and G. E. Illingworth, "Linear Internal Olefins—A Commercial Intermediate for Detergents", CED-/AID Conference on Surfactants, Barcelona, Spain, Mar. 4, 1976).

Other industrial processes commonly used for the production of n-olefins include, for example, the cracking of heavy hydrocarbons and subsequent extraction of the n-olefins by distillation or also the oligomerization of ethylene to obtain α-olefins or internal olefins.

In all cases the n-olefins for industrial use contain paraffins, isoparaffins and/or aromatics in varying quantities depending on the production process used and generally ranging from 0.5 to 5% by weight.

The various phases of which the process of the present invention is composed may be summarized as follows:

(1) Mixing of n-olefins with chloroparaffins, in a molar ratio n-olefins/chloroparaffins of between 70:30 and 99:1, preferably between 80:20 and 98:2.

(2) Reaction of the mixture n-olefins/chloroparaffins with benzene, in the presence of aluminum chloride or aluminum in powder form.

(3) Separation of the hydrocarbon catalytic complex by decanting, washing with aqueous solutions of acids and/or alkalies and then with water until neutral and subsequent fractionated distillation.

In stage (2), the quantity of catalyst used generally ranges from 0.05 to 4.0% in moles with respect to the total quantity of n-olefins and chloroparaffins, whereas the molar ratio benzene/(n-olefins+chloroparaffins) ranges from 1:1 to 20:1, preferably from 3:1 to 15:1. The reaction is generally carried out at a temperature ranging from 20° to 80° C., with a pressure of between 1 and 5 Kg/cm$^2$, for reaction times which generally range from 5 to 180 minutes.

As already mentioned, the process of the present invention, wherein a mixed alkylating agent is used, causes the unexpected formation of sub-products (tetralins, branched alkylbenzenes and high-boiling products) in a much lower quantity with respect to the known processes which use chloropa-raffins or n-olefins alone.

Contrary to the known processes which use n-olefins alone, the hydrocarbon catalytic complex which is formed during the process of the present invention is basically insoluble in the reactive system, and can therefore be easily separated by decanting and possibly, at least in part, recycled. The possibility of recycling the hydrocarbon catalytic complex has a mainly economical advantage in that it enables the part of the catalyst which is still active to be re-used. In addition, the re-integrating aluminum chloride (or metallic aluminum), which is necessary to keep the catalytic activity constant, is added to the reactive system in the presence of the recycled hydrocarbon catalytic complex causing the formation of a highly active catalytic complex, whose reactivity can be easily controlled to guarantee a certain stability in the reactive system.

The high-boiling products obtained as a residue of the fractionated distillation can be, at least partly, recycled in the alkylation stage in such a quantity that the concentration of these high-boiling products in the reaction mixture does not exceed 50% of the total weight n-olefins/chloroparaffins.

The process of the present invention can be batch or preferably continuous. In this respect, it should be pointed out that, according to the present invention, the paraffins present in both the initial chloroparaffins and n-olefins and which are unaltered at the end of the alkylation, can be recycled in the chlorination stage, with the formation of new chloroparaffins. This also enables n-olefins which do not have a high degree of purity, to be used, with obvious economical advantages.

A further advantage arising from the process of the present invention derives from the use of linear alkylbenzenes as surface-active agents. It has in fact been found that the present process produces linear alkylbenzenes characterized by Acid Wash Colour values (determined according to the method ASTMD848-62) which are particularly low and generally lower than those of the corresponding products obtained with the processes known in the art. This is a particularly advantageous result in that colourless products are required in the field of detergents.

These and other advantages of the present invention are more clearly described in the following examples which provide a better illustration of the invention but do not limit it in any way.

EXAMPLE 1

3869 g of anhydrous benzene and 25.1 g of anhydrous AlCl$_3$ are charged into a 10 liter steel reactor (height 40 cm, diameter 18 cm), equipped with a stirrer and thermostatic jacket. After 5 minutes at 20° C., a mixture composed of 837 g of C$_{10}$–C$_{13}$ n-olefins and 1904 g of C$_{10}$–C$_{13}$ chloroparaffins is added.

The n-olefins come from a Pacol-Olex plant and have the following composition (% by weight):
n-olefins C$_{10}$: 10.06%
n-olefins C$_{11}$: 40.75%
n-olefins C$_{12}$: 25.56%
n-olefins C$_{13}$: 19.64%
other hydrocarbons: 3.99%
Titer of n-olefin: 96.01%, of which 0.7% are diolefins.

The chloroparaffins were obtained by the direct chlorination of C$_{10}$–C$_{13}$ n-paraffins with gaseous chlorine at a temperature of 127°–140° C. in a continuous tubular reactor. The composition is the following (% by weight):
n-paraffins C$_{10}$: 9.97%
n-paraffins C$_{11}$: 36.6%
n-paraffins C$_{12}$: 22.84%
n-paraffins C$_{13}$: 19.10%
monochloroparaffins: 12.18%
dichloroparaffins: 0.83%
total chlorine: 2.43%

The molar ratios between the reagents are the following:
benzene/(n-olefins+chloroparaffins): 8:1
AlCl$_3$/(n-olefins+chloroparaffins): 0.02:100
n-olefins/chloroparaffins: 80:20

The reaction is carried out at a temperature of 50° C., with a pressure of 1.1 Kg/cm$^2$, for a period of about 60 min.

The hydrochloric acid formed during the reaction is destroyed by two 500 ml containers arranged in series, each filled with 200 g of an aqueous solution of 10% caustic soda.

The hydrocarbon catalytic complex is then separated by decanting and the resulting mixture of raw alkylate is treated with a 5% solution of NaOH and then with water until neutral. Finally fractionated distillation is carried out, in three columns placed in series: the benzene is separated in the first column, the paraffins and other light hydrocarbons in the second, whereas the linear alkylbenzene is recovered at the head and the high-boiling alkylated products at the bottom of the third column. The paraffins, after being re-integrated with fresh paraffins, are recycled for the chlorination.

The results of the analyses on the final products and the data concerning the mass balances of the reaction are shown in Table I.

EXAMPLE 2

The benzene is alkylated using the same procedure and under the same operating conditions as Example 1, using a mixture of 941.62 g of C$_{10}$–C$_{13}$ n-olefins and 934.1 g of C$_{10}$–C$_{13}$ chloroparaffins as alkylating agent.

The n-olefins and cloroparaffins are the same as Example 1 and are in a molar ratio of 90:10.

The results of the analyses on the final products and the data concerning the mass balances of the reaction are shown in Table I.

The results of the analyses on the final products and the data concerning the mass balances of the reaction are shown in Table I.

TABLE I

| EX | Molar ratio n-olefins/ chloro par. | Conversion (%) | Light products (g/100 g LAB) | Heavy products (g/100 g LAB) | LAB ANALYSIS | | | | |
|---|---|---|---|---|---|---|---|---|---|
| | | | | | Bromine index (mgBr/100 g) (ASTM D1419) | Organic chlorine (ppm) | Linear LAB (%) | 2-phenyl isomer (%) | Tetralins (%) | Acid Wash Color (ASTM D848-62) |
| 1 | 80:20 | ~100 | 2.5 | 8.5 | 30 | 200 | 97.5 | 30.5 | 1.5 | 10.5 |
| 2 | 90:10 | ~100 | 2.4 | 8.4 | 32 | 80 | 98.2 | 31.0 | 0.8 | 10.0 |
| 3 | 95:5 | ~100 | 2.6 | 8.2 | 35 | 50 | 98.8 | 30.4 | <0.5 | 9.5 |
| 4 | 98:2 | ~100 | 2.4 | 7.9 | 30 | <5 | 98.9 | 30.5 | <0.5 | 9.0 |
| 5 | 100:0 | ~100 | 3.0 | 13.2 | 100 | <5 | 98.8 | 30.2 | <0.5 | 11.5 |
| 6 | 100:0 | ~100 | 4.5 | 9.1 | 30 | <5 | 98.5 | 30.3 | 0.6 | 11.0 |
| 7 | 0:100 | ~100 | 2.3 | 15.0 | 80 | 250 | 84.4 | 29.8 | 8.8 | 12.0 |

EXAMPLE 3

The benzene is alkylated using the same procedure and under the same operating conditions as Example 1, using a mixture of 993.9 g of $C_{10}$–$C_{13}$ n-olefins and 467.06 g of $C_{10}$–$C_{13}$ chloroparaffins as alkylating agent. The n-olefins and chloroparaffins are the same as Example 1 and are in a molar ratio of 95:5.

The results of the analyses on the final products and the data concerning the mass balances of the reaction are shown in Table I.

EXAMPLE 4

The benzene is alkylated using the same procedure and under the same operating conditions as Example 1, using a mixture of 1025.29 g of $C_{10}$–$C_{13}$ n-olefins and 186.82 g of $C_{10}$–$C_{13}$ chloroparaffins as alkylating agent. The n-olefins and chloroparaffins are the same as Example 1 and are in a molar ratio of 98:2.

The results of the analyses on the final products and the data concerning the mass balances of the reaction are shown in Table I.

EXAMPLE 5 (COMPARATIVE)

The benzene is alkylated using the same procedure and under the same operating conditions as Example 1, using 1046.2 g of $C_{10}$–$C_{13}$ n-olefins having the same composition as Example 1, as alkylating agent.

The results of the analyses on the final products and the data concerning the mass balances of the reaction are shown in Table I.

EXAMPLE 6 (COMPARATIVE)

The benzene is alkylated using the same procedure and under the same operating conditions as Example 1, using 1046.1 g of $C_{10}$–$C_{13}$ n-olefins, having the same composition as Example 1, as alkylating agent. Before adding the n-olefins, 1.70 g of anhydrous hydrochloric acid, which acts as co-catalyst, are charged into the reactor.

The results of the analyses on the final products and the data concerning the mass balances of the reaction are shown in Table I.

EXAMPLE 7 (COMPARATIVE)

The benzene is alkylated using the same procedure and under the same operating conditions as Example 1, using 9520 g of $C_{10}$–$C_{13}$ chloroparaffins, having the same composition as Example 1, as alkylating agent.

The results of the analyses on the final products and the data concerning the mass balances of the reaction are shown in Table I.

From the results shown in Table I, it is clear that the use of a mixture of n-olefins/chloroparaffins as alkylating agent significantly reduces the formation of heavy products and of tetralins, both with respect to the chloroparaffins and the n-olefins alone. Better results are also obtained as regards the colouring of the final product, as can be seen from the Acid Wash Colour values (measured according the method ASTMD848-62).

EXAMPLE 8

Anhydrous benzene, aluminum metal and a mixture composed of $C_{10}$–$C_{13}$ n-olefins and $C_{10}$–$C_{13}$ chloroparaffins having the same composition as in Example 1 are charged into a vertical tubular reactor, having a ratio height/diameter of 5/1 and equipped with a cooling jacket and stirrer composed of two propellers, one upon the other.

The reaction mixture is kept in the reactor for hour at a temperature of 55° C. The resulting mixture of products is extracted from the top of the reactor and left to decant for about 1 hour. In this way the separation of the hydrocarbon catalytic complex is obtained: one part is recycled in such quantities as to have about 5 parts by weight of the complex in the reactor under steady conditions, whereas the remaining part is sent for disposal.

After washing with an aqueous solution of 10% NaOH by weight and subsequently with water in two columns in series, the raw alkylated product is sent for fractionated distillation. This is carried out in three columns arranged in series: in the first column the benzene is separated, in the second the paraffins and other light hydrocarbons, whereas in the third column the linear alkylbenzene is recovered at the head and the high-boiling alkylated products at the bottom. The paraffins separated in the second column are sent to the chlorination reactor together with the make-up paraffins and chlorine. The high-boiling alkylated products are partly recycled in the alkylation reactor in such quantities as to have about 10 parts of weight of these in the reactor under steady conditions.

When the process is under steady conditions, the composition of the reactive mixture is the following:
$C_{10}$–$C_{13}$ n-olefins: 65.3 parts by weight
$C_{10}$–$C_{13}$ chloroparaffins: 64.8 parts by weight
benzene: 300 parts by weight
aluminum metal in powder form: 0.12 parts by weight
high-boiling alkylated products: 10 parts by weight
hydrocarbon catalytic complex: 5 parts by weight To maintain these ratios of the reactive mixture, the make-up quantities are the following:
$C_{10}$–$C_{13}$ n-olefins: 65.3 parts by weight
$C_{10}$–$C_{13}$ chloroparaffins: 5.5 parts by weight benzene: 33.5 parts by weight
aluminum metal in powder form: 0.12 parts by weight
chlorine: 2.96 parts by weight Under steady conditions, the following are obtained:
linear alkylbenzene: 100 (parts by weight)/hour
high-boiling alkylated products: 3.2 (parts by weight)/hour The linear alkylbenzene produced has the following characteristics:
$C_{10}$–$C_{13}$ linear alkylbenzenes: 98.1% by weight
tetralins: 0.85 by weight
2-phenyl isomer: 30.1 by weight
bromine index (ASTM D1491): 20 mgBr/100 g

We claim:

1. Process for the preparation of linear alkylbenzene which comprises reacting benzene with a mixture composed of n-olefins having from 7 to 20 carbon atoms and chloroparaffins having from 7 to 20 carbon atoms wherein the molar ratio of n-olefins/chloroparaffins is between 70:30 and 99:1 in the presence of a catalyst selected from the group consisting of aluminum chloride or aluminum in powder form.

2. Process according to claim 1, wherein the molar ratio between the n-olefins and chloroparaffins between 80:20 and 98:2.

3. Process according to claims 1 or 2, wherein the molar ratio of benzene/(n-olefins+chloroparaffins) is between 1:1 and 20:1.

4. Process according to claim 3, wherein the molar ratio benzene/(n-olefins+chloroparaffins) is between 3:1 and 15:1.

5. Process according to claim 1 wherein the reaction is carried out at a temperature ranging from 20° to 80° C. and at a pressure of between 1 and 5 Kg/cm$^2$, for a reaction time of between 5 and 180 minutes.

6. Process according to claim 1, wherein the catalyst is used in quantities of between 0.05 and 4% in moles with respect to the total quantity of n-olefins and chloroparaffins.

7. Process according to claim 1 wherein the hydrocarbon catalytic complex formed during the reaction is separated by decanting and the raw alkylated product is subjected after washing with aqueous solutions of acids and/or alkali and water until said raw alkylated product is neutral prior to fractional distillation.

8. Process according to claim 7, wherein the high-boiling products obtained as a residue of the fractional distillation are in par recycled to the alkylation stage in such quantities that the concentration of said high-boiling products in the reaction mixture is not higher than 50% of the total weight of n-olefins/chloroparaffins.

9. (amended) Process according to claim 1 wherein the chloroparaffins are obtained by the partial chlorination of the corresponding paraffins.

10. Process according to claim 9, wherein the paraffins recovered at the end of the alkylation reaction are recycled in the chlorination step.

* * * * *